United States Patent [19]

Greenwald

[11] Patent Number: 5,321,095

[45] Date of Patent: Jun. 14, 1994

[54] AZLACTONE ACTIVATED POLYALKYLENE OXIDES

[75] Inventor: Richard B. Greenwald, Somerset, N.J.

[73] Assignee: Enzon, Inc., Piscataway, N.J.

[21] Appl. No.: 12,447

[22] Filed: Feb. 2, 1993

[51] Int. Cl.$^5$ .................... C08F 283/06; C08G 65/32
[52] U.S. Cl. .................................... 525/404; 525/406; 525/408; 526/260; 548/146; 548/187; 548/204; 548/227; 548/228; 528/327; 528/354; 514/2; 514/4; 514/772.1; 514/772.3; 514/773; 514/785
[58] Field of Search ....................... 525/404, 406, 408; 526/260; 548/146, 187, 204, 227, 228; 528/327, 354

[56] References Cited

U.S. PATENT DOCUMENTS

| | | | |
|---|---|---|---|
| 4,485,236 | 11/1984 | Rasmussen et al. | 548/228 |
| 5,081,197 | 1/1992 | Heilmann et al. | 526/260 |
| 5,157,108 | 10/1992 | Krepski et al. | 525/326.8 |

OTHER PUBLICATIONS

Carter, *Organic Reactions*, vol. III (Adams, ed., John Wiley & Sons, New York 1946), pp. 198–239.
Jones et al., *J. Chem. Soc., (Perkin I)*, 3203–6 (1979).

*Primary Examiner*—Frederick Krass
*Attorney, Agent, or Firm*—Michael N. Mercanti

[57] ABSTRACT

Water-soluble azlactone activated polyalkylene oxides having improved hydrolytic stability and conjugates of the azlactone activated polyalkylene oxides with biologically active nucleophiles are disclosed. Methods of forming and conjugating the activated polyalkylene oxides with biologically active nucleophiles are also disclosed.

9 Claims, No Drawings

AZLACTONE ACTIVATED POLYALKYLENE OXIDES

BACKGROUND OF THE INVENTION

The present invention relates to azlactone activated polyalkylene oxides (PAO's) having improved hydrolytic stability, and to water-soluble polyalkylene oxide conjugates prepared therefrom.

The conjugation of water-soluble polyalkylene oxides with useful molecules such as proteins and polypeptides is well known. The coupling of peptides and polypeptides to polyethylene glycol (PEG) and similar water-soluble polyalkylene oxides is disclosed by U.S. Pat. No. 4,179,337 to Davis et al.

Davis et al. discloses that physiologically active polypeptides modified with PEG exhibit dramatically reduced immunogenicity and antigenicity. Also, the polyalkylene oxide conjugates, when injected into a living organism, have been shown to remain in the bloodstream considerably longer than the corresponding native proteins. Examples of such therapeutic protein conjugates include tissue plasminogen activator, insulin, interleukin II and hemoglobin. In addition, PAO's have also been conjugated to oligonucleotides. See, for example, U.S. Pat. No. 4,904,582.

To conjugate polyalkylene oxides, the hydroxyl endgroups of the polymer must first be converted into reactive functional groups. This process is frequently referred to as "activation" and the product is called an "activated polyalkylene oxide."

Until recently, covalent attachment of the polyalkylene oxide to an appropriate nucleophile was effected by activated polyalkylene oxides such as polyalkylene oxide succinoyl-N-hydroxysuccinimide ester, as disclosed by Abuchowski et al., *Cancer Biochem. Biophys.*, 7, 175–86 (1984). This polyalkylene oxide derivative is desirable because it is reactive under mild conditions.

A shortcoming associated with this derivative, however, is the fact that it is relatively hydrolytically unstable when no nucleophile is present. Recently, in U.S. Pat. No. 5,122,614, polyalkylene oxide-N-succinimide carbonates were disclosed having improved hydrolytic stability over the polyalkylene oxide succinoyl succinates. Even so, the pH conditions necessary to deprotonate the $\epsilon$-NH$_2$ groups of polypeptide lysines for conjugation subject the activated polyalkylene oxide to hydrolysis. This does not affect the reaction end product, other than to reduce its yield. While reduced yields ordinarily affect product cost, the hydrolysis becomes even more costly for several reasons. Firstly, reaction mixtures cannot be prepared significantly in advance. Additional purification of the end product is required to remove the hydrolytic degradation products. Furthermore, the reduction in yield is compensated for by increasing the amount of activated polyalkylene oxide starting material. This increases the viscosity of the reaction mixture, thereby further increasing the processing cost, and potentially interferes with downstream purification of the polymer and conjugate.

A need exists, therefore, for polyalkylene oxides that are unreactive towards weak nucleophiles such as water but react readily with stronger nucleophiles such as polypeptides. While azlactones have been reported to react readily with amines and less readily with water, azlactone activated PAO's are unreported. Unsaturated azlactones, in particular, are not altered by long contact with water. See, Carter, *Organic Reactions*, Vol. III (Adams, ed., John Wiley & Sons, New York 1946) pp. 198–239. The disclosed unsaturated azlactones have the following structures

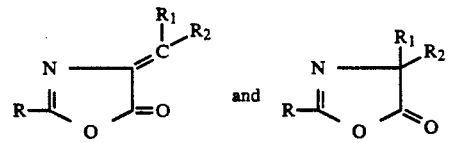

in which R$_1$ and R$_2$ are independently selected from hydrogen, phenyl rings and lower alkyl moieties. R is the residue of an $\alpha$-acyl amino acid.

SUMMARY OF THE INVENTION

It has now been discovered that certain azlactone substituted polyalkylene oxides possess a desirable combination of nucleophilic reactivity and hydrolytic stability. For the conjugation of polyalkylene oxides with bioactive materials, the desired aminolysis predominates over hydrolysis, so that reactions in aqueous solutions occur with higher yields. The azlactone activated polyalkylene oxides have improved resistance to hydroxyl attack under the pH conditions which are required in order to deprotonate the protein amines.

The water-soluble azlactone activated polyalkylene oxides of the present invention include unsaturated azlactone activated polyalkylene oxides, represented by the structure of Formula IA:

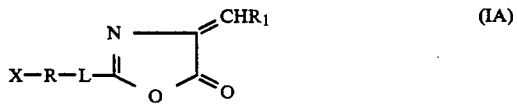

wherein

L is selected from —O—, —CH$_2$— and amino acid and polypeptide residues;

R is a water-soluble polyalkylene oxide;

R$_1$ is a moiety selected from hydrogen, alkyl and cycloalkyl moieties, carbocyclic and heterocyclic aromatic rings, and $\alpha,\beta$-unsaturated alkyl moieties; and X is a terminal moiety of the polyalkylene oxide.

The water-soluble azlactone activated polyalkylene oxides of the present invention also include saturated azlactone activated polyalkylene oxides, represented by the structure of Formula IB:

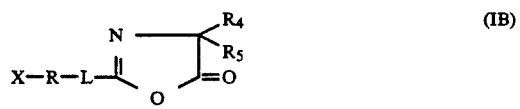

wherein L, R and X are the same as described above with respect to Formula IA and R$_4$ and R$_5$ are moieties independently selected from hydrogen, alkyl, aryl and alkylaryl moieties. The saturated azlactone activated polyalkylene oxides having the structure of Formula IB in which R$_4$ and R$_5$ are both hydrogen do not have significantly improved hydrolytic stability, but are useful intermediates in the preparation of the unsaturated azlactone activated polyalkylene oxides of Formula IA.

Therefore, in accordance with the present invention, water-soluble azlactone activated polyalkylene oxides are provided. The azlactone activated polyalkylene oxides of the present invention include the unsaturated azlactones of Formula IA and the saturated azlactones of Formula IB. The saturated azlactones of Formula IB include species in which both of $R_1$ and $R_2$ are hydrogen.

One process for forming the unsaturated azlactone-activated polyalkylene oxides of Formula IA reacts an α-acyl amino acid terminated polyalkylene oxide with an aromatic or unsaturated aliphatic aldehyde in the presence of acetic anhydride. Therefore, in accordance with the present invention there is provided a process for the preparation of water-soluble unsaturated azlactone activated polyalkylene oxides, which process includes the steps of:

providing an α-acyl amino acid terminated polyalkylene oxide having a structure corresponding to Formula II:

$$X-R-L-CO-NH-CH_2-COOH \quad (II)$$

and reacting the amino acid terminated polyalkylene oxide with acetic anhydride and an aldehyde having a structure corresponding to Formula III:

$$R_1-C=O \quad (III)$$

so that an unsaturated azlactone activated polyalkylene oxide is formed having a structure corresponding to Formula IA, in which R, L and X are the same as described above with respect to Formula IA. For this process, $R_1$ is selected from carbocyclic and heterocyclic aromatic rings and α, β-unsaturated alkyl moieties.

Alternatively, the amino acid terminated polyalkylene oxide of Formula II may first be reacted with acetic anhydride to form the saturated azlactone substituted polyalkylene oxide of Formula IB in which both $R_4$ and $R_5$ are hydrogen. The saturated azlactone may be recovered at this point as a useful intermediate in the preparation of the unsaturated azlactones of Formula IA, or it may be further reacted with the aldehyde of Formula III to form the unsaturated azlactone activated polyalkylene oxide of Formula IA in which $R_1$ is selected from carbocyclic and heterocyclic aromatic rings and α,β-unsaturated alkyl moieties.

The unsaturated azlactone activated polyalkylene oxides of Formula IA may also be formed by the reaction of an α-acyl-β-hydroxy, alkoxy or alkyl ester amino acid terminated polyalkylene oxide with acetic anhydride. Therefore, in accordance with the present invention there is provided still another process for the preparation of water-soluble unsaturated azlactone activated polyalkylene oxides, which process includes the steps of:

providing an α-acyl amino acid terminated polyalkylene oxide having a structure corresponding to Formula IIA:

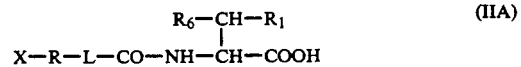

$$\begin{array}{c} R_6-CH-R_1 \\ | \\ X-R-L-CO-NH-CH-COOH \end{array} \quad (IIA)$$

and reacting the amino acid terminated polyalkylene oxide with acetic anhydride so that an azlactone activated polyalkylene oxide is formed having a structure corresponding to Formula IA, wherein R, $R_1$, L and X are the same as described above with respect to Formula IA. $R_6$ is a moiety selected from hydroxyl, alkoxy and alkyl ester moieties.

The saturated azlactone activated polyalkylene oxides of Formula IB in general are formed by reacting a α-acyl amino acid terminated polyalkylene oxide with acetic anhydride. Therefore, in accordance with the present invention there is provided a process for the preparation of water-soluble saturated azlactone activated polyalkylene oxides, which process includes the steps of:

providing an α-acyl amino acid terminated polyalkylene oxide having a structure corresponding to Formula IIB:

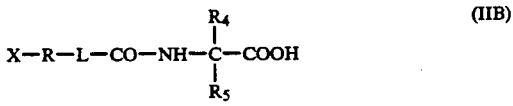

$$\begin{array}{c} R_4 \\ | \\ X-R-L-CO-NH-C-COOH \\ | \\ R_5 \end{array} \quad (IIB)$$

and reacting the amino acid terminated polyalkylene oxide with acetic anhydride so that a saturated azlactone activated polyalkylene oxide is formed having a structure corresponding to Formula IB in which R, L and X are the same as described above with respect to Formula IA and $R_4$ and $R_5$ are moieties independently selected from hydrogen, alkyl, aryl and alkylaryl moieties.

The azlactone activated polyalkylene oxides of the present invention react with biologically active nucleophiles to form covalently bonded conjugates thereof. When the biologically active nucleophile is a protein or polypeptide, conjugation occurs at the ε—$NH_2$ moieties of lysines.

The present invention therefore also provides a method of forming a biologically active conjugate of a biologically active nucleophile and one or more water-soluble polyalkylene oxides covalently bonded thereto, which method includes the steps of:

contacting a biologically active nucleophile with an azlactone activated polyalkylene oxide, so that a biologically active conjugate of the biologically active nucleophile and the polyalkylene oxide is formed; and recovering the biologically active conjugate.

The present invention therefore also includes a biologically active conjugate of a biologically active nucleophile and one or more water-soluble polyalkylene oxides covalently bonded thereto by a linkage formed by reacting the nucleophile with an azlactone activated polyalkylene oxide.

The biologically active conjugates of the present invention possess numerous therapeutic applications. Therefore, there is also included in the present invention a method of treatment in which a mammal in need thereof is administered a therapeutically effective amount of the biologically active conjugates of the present invention.

The hydrolytic stability of the azlactone activated polyalkylene oxides of the present invention permit bulk solutions of activated polyalkylene oxide to be prepared in advance of production runs. Furthermore, the azlactone group can be reacted with a variety of biologically active nucleophiles of interest other than lysine ε-amino groups of polypeptides. For example, the azlactone activated polyalkylene oxides of the present invention will react with any primary or secondary amino group. The azlactones will also react with other nucleophilic peptide groups, such as α-amino groups, guanidino moieties, mercapto groups, and the like, at the appropriate pH. In addition, the azlactones are also reactive with nucleotides such as guanine, adenine, and the like, and derivatives thereof which possess nucleophilic amino groups.

DETAILED DESCRIPTION OF THE PREFERRED EMBODIMENT

The azlactone activated polyalkylene oxides of the present invention are preferably prepared from polyalkylene oxides that are soluble in water at room temperature. Polyalkylene oxides meeting this requirement are polyethylene glycol (PEG) and copolymers thereof. Block copolymers of PEG with polypropylene glycol or polypropylene oxide are also suitable for use with the present invention, provided that the degree of block copolymerization is not so great as to render the polymer insoluble in water at room temperature. Other polymers suitable for use with the present invention include polyacrylates, polymethacrylates and polyvinyl alcohols.

The molecular weight of the polyalkylene oxide will depend mainly upon the end use of a particular polymer conjugate. Those of ordinary skill in the art are capable of determining molecular weight ranges suitable for their end-use applications. In general, the useful range of molecular weight is a number average molecular weight between about 600 and about 100,000 daltons, and preferably between about 2,000 and about 20,000 daltons. A molecular weight of 5,000 daltons is most preferred.

Preferred azlactone activated polyalkylene oxides are represented by the structures of Formula IA and IB, wherein R is a water-soluble polyalkylene oxide, L is selected from —O—, —CH$_2$—, amino acid and peptide residues; R$_1$ is a moiety selected from hydrogen, alkyl, phenyl, phenylalkyl and cycloalkyl moieties, and X is a terminal moiety of the polyalkylene oxide.

X can be a group into which a terminal hydroxyl group may be converted, including the reactive derivatives of the prior art disclosed in U.S. Pat. Nos. 4,179,337, 4,847,325, 5,122,614 and in copending and commonly owned U.S. patent application Ser. No. 626,696, filed Mar. 18, 1991, now U.S. Pat. No. 5,193,354 the disclosures of all of which are hereby incorporated herein by reference thereto. The heterobifunctional polymers can be prepared by methods known to those skilled in the art without undue experimentation. When the moieties selected for L and R$_1$ on both ends of the polymer are identical, the polymer will then be a symmetrical, homobifunctional polymer derivative.

Such double polymer substitution can result in either intra- or intermolecular crosslinking of the nucleophile, which, in some cases, can be useful. Such crosslinking can be controlled by the amount of polymer used and the concentration of reacting species, which methods are well-known to those of ordinary skill in the art.

Crosslinking can also be prevented by using a preblocked polymer having only one labile hydroxyl group per polymer moiety. In such polymers, X would represent a blocking group such as an alkoxy group of one to four carbon atoms. The preferred blocking group is a methoxy group. For the preparation of homobifunctional and monofunctional polymer derivatives, see Buckmann et al., *Makromol. Chem.*, 182(5), 1379-84 (1981). X can also represent an antibody or solid support covalently coupled to the polymer by methods known to those skilled in the art as illustrated in EP 295,073.

L is preferably —O— or —CH$_2$—. When L is an amino acid or peptide residue, L preferably contains between 1 and 20 amino acids, and more preferably between 1 and 4 amino acids. The amino acids are preferably naturally occurring amino acids. The terminal amino group is positioned opposite the azlactone ring.

The unsaturated azlactone activated polyalkylene oxides of Formula IA, in which R$_1$ is selected from carbocyclic and heterocyclic aromatic rings and $\alpha,\beta$-unsaturated alkyl moieties are formed by reacting the aldehyde of Formula III in a reaction mixture containing acetic anhydride and the $\alpha$-acyl amino acid substituted polyalkylene oxide of Formula II, in which X, L and R are the same as described above with respect to Formula IA. The resulting azlactone is hydrolytically stable, yet reacts readily with stronger nucleophiles in a ring-opening reaction. R$_1$ is preferably an aromatic ring selected from benzene, naphthalene, pyrene, biphenyl, thiophene, furan, pyrrole, indole, chromane, coumarone and thiazole rings. The rings may be substituted or unsubstituted. Preferred substituents include haloalkyl, hydroxyl, alkoxy, acyloxy, carbethoxy and nitro moieties and combinations thereof.

The unsaturated azlactone activated polyalkylene oxides of Formula IA may also be formed by first reacting the $\alpha$-acyl amino acid substituted polyalkylene oxide of Formula II, with acetic anhydride to obtain the saturated azlactone substituted polyalkylene oxide of Formula IB in which R$_4$ and R$_5$ are both hydrogen. The resulting product represents an intermediate in the synthesis of the unsaturated azlactone activated polyalkylene oxides of Formula IA. The saturated azlactone can then be reacted with the aldehyde of Formula III to form the unsaturated azlactone-activated polyalkylene oxides of Formula IA, in which R$_1$ is selected from carbocyclic and heterocyclic aromatic rings and $\alpha,\beta$-unsaturated alkyl moieties.

Acetic anhydride, when present, is utilized as the reaction solvent. Otherwise, the reaction is carried out in a non-hydroxylic solvent in which the reactants are soluble, such as toluene. A reaction temperature between about 75° C. and about 110° C. is suitable, and a temperature between about 95° C. and about 100° C. is preferred. All materials must be essentially free of water. Scrupulous care must be taken not to contaminate the reaction mixture with water.

The polyalkylene oxides of Formula II are formed by one of two methods. In the first method, a hydroxyl-terminated polyalkylene oxide is reacted with an isocyanate-substituted compound selected so that the resulting compound corresponds to an amino acid or peptide sequence coupled to a polyalkylene oxide via a urethane linkage. Thus, ethyl isocyanatoacetate will form a —O—CO-glycine ethyl ester terminated polyalkylene oxide, which can be converted to the carboxylic acid using well-known techniques. Ethyl 3-isocyanatopropionate will form a —O—CO—$\beta$-alanine ethyl ester terminated polyalkylene oxide. This reaction is carried out in a non-hydroxyl solvent in which the reactants are soluble, such as toluene. Again, the reaction mixture should not be contaminated with water. Reaction temperatures between 10° C. and 50° C. are suitable, and temperatures between 20° C. and 30° C. are preferred.

The ethyl isocyanoacetate product represents the polyalkylene oxide of Formula II in which L is —O—. The —O—CO-amino acid or —O—CO-peptide sequence terminated reaction product can be extended by coupling additional amino acids or peptide sequences to the reaction product by well-known reactions utilizing coupling reagents such as carbodiimides. (See Bodenszky, *Principles of Peptide Synthesis* (Springer-Verlag, New York, 1984)). Formula II requires that the terminal amino acid be glycine.

In the second method, a polyalkylene oxide carboxylic acid or acid chloride is reacted with an amino acid or peptide sequence. Polyalkylene oxide carboxylic acids and acid chlorides can be prepared by the method disclosed by Buckmann et al., *Makromol Chem.*, 182(5), 1379-84 (1981), or by the method of U.S. Pat. No. 5,122,614, the disclosure of Which is hereby incorporated herein by reference thereto. This reaction is also carried out utilizing well-known techniques in a non-hydroxyl solvent such as toluene. When the carboxylic acid is utilized, the reaction should be mediated with a coupling reagent such as a carbodiimide. (Again, See Bodanszky, *Principles of Peptide Synthesis*.) Reaction temperatures between 4° C. and 40° C. are suitable, and temperatures between 10° C. and 20° C. are preferred. Once more, care should be taken not to contaminate the reaction mixture with water.

When the amino acid is glycine, the reaction product represents the polyalkylene oxide of Formula II in which L is —CH$_2$—. Again, the amino acid or peptide sequence terminated reaction product can be extended by coupling additional amino acids or peptide sequences according to the method of Bodanszky, *Principles of Peptide Synthesis*, provided that the terminal amino acid is glycine.

The unsaturated azlactone activated polyalkylene oxides of Formula IA may also be formed by reacting the α-acyl amino acid terminated polyalkylene oxide of Formula IIA with acetic anhydride. X, L, R and R$_1$ are the same as described above with respect to Formula IA and II. R$_6$ is a moiety selected from hydroxyl, alkoxy and alkyl ester moieties.

The polyalkylene oxides of Formula IIA are also formed by the methods utilized in the preparation of the polyalkylene oxides of Formula II. However, instead of glycine, the terminal amino acid has a structure corresponding to Formula IV:

in which R$_1$ is the same as described above with respect to Formula IIA, and R$_6$ is a hydroxyl, alkoxy or alkyl ester moiety.

As will be readily appreciated, Formula IV includes naturally occurring protein amino acids such as serine, threonine and the alkyl ester of aspartic acid.

The saturated azlactone activated polyalkylene oxides of Formula IB are formed by reacting the α-acyl amino acid terminated polyalkylene oxide of Formula IIB with acetic anhydride. X, R and L are the same as described above with respect to Formula IA. R$_4$ and R$_5$ are independently selected from hydrogen, alkyl, aryl and alkylaryl moieties.

The polyalkylene oxides of Formula IIB are also formed by the methods utilized in the preparation of the polyalkylene oxides of Formula II. The terminal amino acid has a structure corresponding to Formula II:

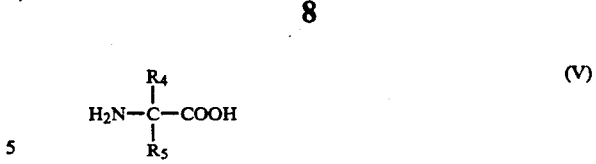

in which R$_4$ and R$_5$ are the same as described above with respect to Formula IIB.

As will be readily appreciated, when R$_4$ and R$_5$ are both hydrogen, the structure of Formula V represents glycine, which is thus a suitable terminal amino acid in this embodiment of the invention. Formula V also includes naturally occurring protein amino acids such as alanine, isoleucine, leucine, methionine, phenylalanine, serine, threonine, thyroxine, tyrosine and valine.

The azlactone activated polyalkylene oxides are purified from low molecular weight materials by conventional methods. The azlactone can then be reacted with biologically active nucleophiles to form a hydrolytically stable linkage between the polyalkylene oxide and the biologically active nucleophile. The resulting product represents a biologically active conjugate of the nucleophile and the polyalkylene oxide.

The term "hydrolytically stable" means that the azlactones of the present invention, in aqueous solution, will not undergo substantial degradation at physiological pH and at temperatures up to 27° C. Degradation of less than 50% under these conditions over an eight hour time period is considered insubstantial.

The term "biologically active" is used with respect to the nucleophiles of the present invention consistently with the meaning commonly understood to those of ordinary skill in the art, which meaning is not limited to physiological or pharmacological activities of the nucleophiles in the therapeutic sense. For example, many physiologically active nucleotides such as enzymes, the polyalkylene oxide conjugates of which may not have therapeutic applications, are able to catalyze reactions in organic solvents. Likewise, regardless of the therapeutic uses for polyalkylene oxide conjugates of proteins such as concanavalin A, immunoglobulins, and the like, the polyalkylene oxide conjugates of these proteins are also useful as laboratory diagnostic tools.

The polyalkylene oxide conjugates of the biologically active nucleophiles of the present invention are biologically active and possess numerous therapeutic applications. Mammals in need thereof may be treated by administering a therapeutically effective amount of the biologically active polyalkylene oxide conjugates of the biologically active nucleophiles of the present invention.

Therefore, the biologically active nucleophiles of interest to the present invention include a variety of enzymes, including, but not limited to, carbohydrate-specific enzymes, proteolytic enzymes, and the like. Enzymes of interest, for both biological applications in general and therapeutic applications in particular include the oxidoreductases, transferases, hydrolases, lyases, isomerases and ligases disclosed by U.S. Pat. No. 4,179,337, the disclosure of which is hereby incorporated herein by reference thereto. Without being limited to particular enzymes, examples of specific enzymes of interest include asparaginase, arginase, adenosine deaminase, superoxide dismutase, catalase, chymotrypsin, lipase, uricase and bilirubin oxidase. Carbohydrate-specific enzymes of interest include glucose oxidase, glucosidase, galactosidase, glucocerebrosidase, glucuronidase, etc.

The biologically active nucleophiles of the present invention also include proteins of general biological or therapeutic interest, including, but not limited to, hemoglobin and serum proteins such as Factor VIII, Factor IX, immunoglobulins, lectins, interleukins, interferons and colony stimulating factors, and ovalbumin and bovine serum albumin (BSA). Other proteins of general biological or therapeutic interest include hormones such as insulin, ACTH, glucagon, somatostatin, somatotropins, thymosin, parathyroid hormone, pigmentary hormones, somatomedins, erythropoietin, luteinizing hormone, hypothamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Certain of the above proteins such as the interleukins, interferons and colony stimulating factors also exist in non-glycosilated form, usually the result of preparation by recombinant protein techniques. The non-glycosilated versions are also among the biologically active nucleophiles of the present invention.

Other proteins of interest are allergen proteins disclosed by Derborg et al., *Crit. Rev. Therap. Drug Carrier Syst.*, 6, 315–65 (1990) as having reduced and consequently suitable for use as tolerance inducers. Among the allergins disclosed are ragweed Antigen E, honeybee venom, mite allergen, and the like.

Other biologically active nucleophiles of the present invention include antibodies, antibody fragments, single chain antigens, nucleotides and oligonucleotides. The coupling of oligonucleotides to polyalkylene oxides is disclosed by the above-cited U.S. Pat. No. 4,904,582. Still other biologically active nucleophiles included within the scope of the invention are therapeutically active nucleophilic compounds. Of the therapeutically active nucleophilic compounds, chemotherapeutic molecules having appropriately reactive nucleophilic moieties are particularly preferred. For example, anti-tumor agents, anti-infective agents, and the like, or, in general, pharmaceutical chemicals containing an appropriate nucleophilic group, are included within the scope of the present invention.

One or more polyalkylene oxides can be attached covalently to the biologically active nucleophile by reacting the polyalkylene oxide azlactone with the nucleophile. The azlactone reacts with the nucleophile in a ring-opening reaction to form a linkage covalently bonding the nucleophiles to the polyalkylene oxide. When the nucleophile is a protein or polypeptide, conjugation occurs at the $\epsilon$-NH$_2$ moieties of lysines to form linkages containing stable glycine moieties.

For nucleophiles such as polypeptides, more than one polyalkylene oxide conjugate per nucleophile is preferred. The degree of conjugation is limited only by the number of $\epsilon$-NH$_2$ moieties of lysines. The optimum degree of conjugation can be readily determined for a particular nucleophile by one of ordinary skill in the art without undue experimentation. The degree of conjugation may be modified by varying the reaction stoichiometry using well-known techniques.

The reaction of azlactone activated polyalkylene oxides with the $\epsilon$-NH$_2$ moieties of polypeptide lysines is illustrated by the reaction sequence depicted below with the unsaturated azlactone activated polyalkylene oxide of Formula IB, in which R, L, X and R$_4$ and R$_5$ are the same as described above with respect to Formula IA and R$_3$ represents the balance of the polypeptide:

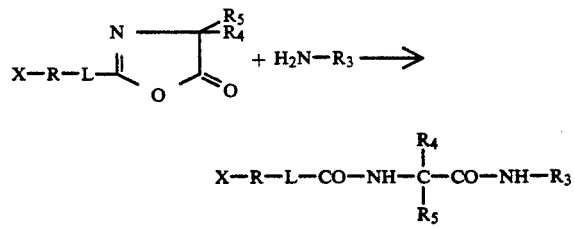

The unsaturated azlactone activated polyalkylene oxide of Formula IA reacts similarly.

The biologically active nucleophiles may be reacted directly with the azlactone activated polyalkylene oxides in an aqueous reaction medium. This reaction medium may also be buffered, depending upon the pH requirements of the nucleophile. The optimum pH for the reaction is generally between about 6.5 and about 8.0 and preferably about 7.4.

In all instances, the optimum reaction medium pH for the stability of particular nucleophiles and for reaction efficiency, and the buffer in which this can be achieved, is readily determined within the above ranges by those of ordinary skill in the art without undue experimentation. For purposes of this application, the operativeness of the within reactions under mild conditions is defined as meaning that the preferred temperature range is between about 4 and about 37° C.

Those of ordinary skill in the art will understand that the reactions will run somewhat faster to completion at higher temperatures, with the proviso that the temperature of the reaction medium cannot exceed the temperature at which the nucleophile may denature or decompose. Furthermore, those of ordinary skill in the art will understand that certain nucleophiles, particularly polypeptides, will require reaction with the azlactone activated polyalkylene oxides at reduced temperatures to minimize loss of activity and/or to prevent denaturing. The reduced temperature required by particular polypeptides is preferably no lower than 4° C. and in no event should this temperature be lower than 0° C. The reaction will still take place, although longer reaction times may be necessary.

Usually, the nucleophile is reacted in aqueous solution with a quantity of the azlactone activated polyalkylene oxide in excess of the desired degree of conjugation. Following the reaction, the conjugated product is recovered and purified by diafiltration, column chromatography or the like.

In view of the foregoing, it can be readily appreciated that the azlactone activated polyalkylene oxides of the present invention possess the optimum balance of reactivity and hydrolytic stability so that polymer conjugates can be formed with biologically active nucleophiles with an insubstantial amount of hydrolytic degradation of the activated polyalkylene oxide. Thus, reaction yields are increased and process costs are reduced.

The following non-limiting examples illustrate certain aspects of the invention. All parts and percentages are by weight unless otherwise noted, and all temperatures are in degrees Celsius.

EXPERIMENTAL

Example 1

Preparation of m-PEG-β-Alanine

A β-alanine substituted poly(ethylene glycol) monomethyl ether) (m-PEG) is prepared for coupling with glycine. The m-PEG-β-alanine-glycine to be prepared corresponds to the amino acid substituted polyalkylene oxide of Formula II in which X is methoxy, R is PEG and L is —O—CO—NH—CH$_2$—CH$_2$—. The m-PEG is β-alanine substituted by adding 100 g (20 mmol.) m-PEG-OH (Union Carbide) to 700 mL of toluene. The m-PEG-OH has a number average molecular weight of 5,000 daltons. The solution is refluxed for four hours, under nitrogen, in a flask equipped with a Dean-Stark trap. During this time, a total of 200 mL of solvent is removed from the trap. The reaction mixture is then cooled to 40° C, followed by the addition of ethyl 3-isocyanatopropionate (7.2 g, 50 mmol.) and Sn(II) octoate (0.3 g) (Aldrich Chemical Co.). The reaction mixture is maintained at 40° C. for 16 hours. Removal of solvent and recrystallization from one liter of 2-propanol gave 93 g (93 percent) of the m-PEG-β-alanine ethyl ester. The $^1$H and $^{13}$C NMR spectra are consistent with the structure.

The m-PEG-β-alanine ethyl ester (77 g, 15 mmol.) is dissolved in 500 mL of water and to this solution is added 5 g (125 mmol.) of sodium hydroxide. The pH of the solution is 11.75. The solution is allowed to stir at room temperature for 2.5 hours and then acidified with HCl to pH 2-3. After dissolving 125 g NaCl, the reaction mixture is extracted with two 250 mL portions of methylene chloride. The extract is dried over MgSO$_4$, followed by solvent evaporation, and recrystallization from 750 mL 2-propanol, wherein 73 g (95 percent) m-PEG-β-alanine is obtained. Both $^1$H and $^{13}$C NMR spectra showed the disappearance of the ethyl group of the ester.

Example 2

Preparation of m-PEG-β-Alanine-Glycine

The m-PEG-β-alanine of Example 1 (5.1 g, 1 mmol.) is dissolved in 50 mL of pH 5.5 acetate buffer, and to the solution are added 21 mg (1.1 mmol.) of 1-(3-dimethylaminopropyl)-3-ethylcarbodiimide hydrochloride (EDC) and 280 mg (2.0 mmol.) of glycine ethyl ester hydrochloride (Aldrich Chemical Co.). The reaction mixture is stirred for two hours and the pH is maintained at 5.5 by the addition of 0.1 N HCl. The product is isolated by extraction with methylene chloride, followed by drying over MgSO$_4$, solvent evaporation and recrystallization from 2-propanol as in the case of m-PEG-β-alanine of Example I. The ester group is removed by hydrolysis with 0.25 M NaOH as in Example I for m-PEG-β-alanine. The $^1$H and $^{13}$C NMR spectra are consistent with the structure.

Example 3

Preparation of an Unsaturated Azlactone

The m-PEG-β-alanine-glycine of Example 2 (2.6 g, 0.50 mmol.), benzaldehyde (58 mg, 0.55 mmol.), sodium acetate (45 mg, 0.55 mmol.), and acetic anhydride (168 mg, 1.65 mmol.) are heated in a water bath at 80° C. for thirty minutes. The reaction mixture is poured into 20 mL ice water and extracted with methylene chloride, dried over MgSO$_4$ and concentrated according to the work-up procedure of Example I. The pure product is then precipitated with ether and dried under high vacuum. The product is characterized by IR and NMR, and the spectral data are consistent with the structure of the unsaturated azlactone activated polyalkylene oxide of Formula IA in which X is methoxy, R is PEG, L is —O—CO—NH—CH$_2$—CH$_2$— and R$_1$ is a phenyl moiety.

Example 4

Preparation of m-PEG-Glycine with a Urethane Linkage

A glycine substituted m-PEG was prepared, corresponding to the amino acid substituted polyalkylene oxide of Formula II in which X is methoxy, R is PEG and L is —O—. The m-PEG was glycine substituted by first drying 50 g (10 mmol.) m-PEG-OH (Union Carbide) as in Example 1. The 5,000 dalton number average molecular weight polymer was used again. The dried toluene solution is cooled to 40° C., followed by the addition of ethyl isocyanatoacetate (1.7 g, 15 mmol.) to obtain m-PEG-glycine ethyl ester, which is hydrolyzed by 0.25 N sodium hydroxide to m-PEG-glycine, and then worked up and isolated following the procedures of Example 1. The product is characterized by IR and NMR, and the spectral data are consistent with the structure.

Example 5

Preparation of a Saturated Azlactone

The m-PEG-glycine of Example 4 (5.1 g, 1.0 mmol.) is added to 50 mL of acetic anhydride and heated in a water bath at 100° C. for ten minutes. The reaction mixture is poured into an ice water bath and the pure product is isolated and worked up as described in Example 3. The product is characterized by IR and NMR, and the spectral data are consistent with the structure of the saturated azlactone activated polyalkylene oxide of Formula IB in which X is methoxy, R is PEG, L is —O— and R$_4$ and R$_5$ are both hydrogen.

Example 6

Preparation of an Unsaturated Azlactone

The saturated azlactone of Example 5 (5.1 g, 1.0 mmol.) and benzaldehyde (120 mg, 1.1 mmol.) are added to 50 mL of methylene chloride and heated in a water bath at 35° C. for 60 minutes. The reaction mixture is quenched and the unsaturated azlactone is isolated and worked up as in Example 3. The IR and NMR spectra are consistent with the structure of the unsaturated azlactone activated polyalkylene oxide of Formula IA in which X is methoxy, R is PEG, L is —O— and R$_1$ is a phenyl moiety.

Example 7

Conjugation of an Unsaturated Azlactone with Hemoglobin

The unsaturated azlactone activated polyalkylene oxide of Example 6 is conjugated with bovine hemoglobin by first preparing a 10 mL solution of pH 7.8 phosphate buffer by dissolving 0.1380 g NaH$_2$PO$_4$.H$_2$O, 0.2681 g Na$_2$HPO$_4$·7H$_2$O and 0.2338 g NaCl in 7.0 mL deionized water. The pH of this solution is then adjusted to 7.8 with 1.0 N NaOH and diluted to 10 mL with deionized water. A 4.0 mL sample of isolated bovine hemoglobin (10.9 percent, 7.02×10$^{-3}$ mmol.) is measured into a 50 mL jacketed beaker chilled to 4° C. by means of a refrigerated recirculating bath. A thermometer and pH electrode were placed in the hemoglobin solution, which is stirred magnetically. The pH of the hemoglobin is adjusted to 7.8 with 1.0 N NaOH or 1.0 N HCl as necessary.

To this is added 0.65 g of the unsaturated azlactone of Example 6 (0.13 mmol.) followed by 4.0 mL of the pH 7.8 phosphate buffer prepared above. The mixture is allowed to stir at 4° C. for one hour while maintaining pH 7.8 with dropwise additions of 1.0 N NaOH or 1.0 N HCl. After one hour of reaction time, 42 mg (0.24 mmol.) of cysteine HCl is added, followed by 9.5 mg (0.13 mmol.) of glycine. The pH is adjusted up to 7.8 using 1.0 N NaOH, and the mixture is allowed to stir for 15 minutes. The product is stored in a 4° C refrigerator. The final hemoglobin concentration of the product was about 5 percent. Capillary zone electrophoresis results indicate that PEG conjugation of the hemoglobin was effected by this procedure.

Example 8

Preparation of m-PEG-$\beta$-Alanine-Alanine m-PEG-$\beta$-alanine-alanine is prepared following the procedure utilized to prepare the m-PEG-$\beta$-alanineglycine of Example 2, substituting 0.307 mg (2.0 mmol.) of alanine ethyl ester hydrochloride (Aldrich Chemical Co.) for the glycine ethyl ester hydrochloride. Following removal of the ester group, the $^1$H and $^{13}$C NMR spectra are consistent with the structure of the amino acid substituted polyalkylene oxide of Formula IIB in which X is methoxy, R is PEG, L is —O—CO—NH—CH$_2$—CH$_2$—, R$_4$ is methyl and R$_5$ is hydrogen.

Example 9

Preparation of a Saturated Azlactone

The m-PEG-$\beta$-alanine-alanine of Example 8 (2.6 g, 0.5 mmol.) is added to 50 mL of acetic anhydride and heated in a water bath at 100° C. for ten minutes. The reaction mixture is poured into 200 mL ice water and stirred for twenty minutes. The product is isolated by extraction with two 100 mL portions of methylene chloride. The extract is dried over MgSO$_4$, concentrated, precipitated with ether, and dried under high vacuum as in the procedure of Example 3. The product is characterized by IR and NMR, and the spectral data are consistent with the structure of the saturated azlactone activated polyalkylene oxide of Formula IB in which X is methoxy, R is PEG, L is —O—CO—NH—CH$_2$—CH$_2$—, R$_4$ is methyl and R$_5$ is hydrogen.

As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A water-soluble, hydrolytically-stable, azlactone-activated polyalkylene oxide, comprising a structure represented by:

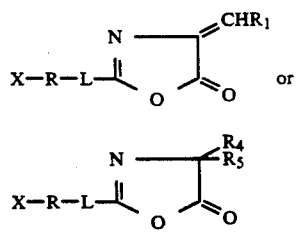

wherein
R represents the non-terminal portion of a water-soluble polyalkylene oxide having a number average molecular weight between about 600 and about 100,000 daltons;
L is selected from the group consisting of —O— and —CH$_2$—;
R$_1$ is a moiety selected from the group consisting of hydrogen, alkyl and cycloalkyl moieties, carbocyclic and heterocyclic aromatic rings and $\alpha$, $\beta$-unsaturated alkyl moieties;
R$_4$ and R$_5$ are moieties independently selected from the group consisting of hydrogen, alkyl, aryl and alkylaryl moieties; and
X is a terminal moiety of said polyalkylene oxide selected from the group consisting of alkoxy moieties containing up to four carbon atoms.

2. The azlactone-activated polyalkylene oxide of claim 1, wherein R$_1$ is an aromatic ring selected from the group consisting of substituted and unsubstituted benzene, mapthalene, pyrene, biphenyl, thiophene, furan, pyrrole, indole, chromane, coumarone and thiazole rings.

3. The azlactone-activated polyalkylene oxide of claim 1, wherein X is a methoxy moiety.

4. The azlactone activated polyalkylene oxide of claim 1, wherein at least one of R$_4$ and R$_5$ is a moiety selected from the group consisting of alkyl, aryl and alkylaryl moieties.

5. The azlactone activated polyalkylene oxide of claim 1, wherein both R$_4$ and R$_5$ are hydrogen.

6. The azlactone-activated polyalkylene oxide of claim 1, wherein said polyalkylene oxide is selected from the group consisting of polyethylene glycol and block copolymers of polyethylene glycol and polypropylene glycol.

7. The azlactone-activated polyalkylene oxide of claim 6, wherein said polyalkylene oxide is polyethylene glycol.

8. The azlactone-activated polyalkylene oxide of claim 1, wherein said polyalkylene oxide has a number average molecular weight between about 2,000 and about 20,000 daltons.

9. The azlactone-activated polyalkylene oxide of claim 8, wherein said polyalkylene oxide has a 5,000 dalton number average molecular wight.

* * * * *